United States Patent
Assmann et al.

(10) Patent No.: US 7,742,798 B2
(45) Date of Patent: Jun. 22, 2010

(54) METHOD AND MRT APPARATUS FOR EVALUATION OF A CINEMATOGRAPHIC IMAGE SERIES OF THE HEART

(75) Inventors: Stefan Assmann, Erlangen (DE); Renate Jerecic, Chicago, IL (US)

(73) Assignee: Siemens Aktiengesellschaft, Munich (DE)

( * ) Notice: Subject to any disclaimer, the term of this patent is extended or adjusted under 35 U.S.C. 154(b) by 627 days.

(21) Appl. No.: 11/504,488

(22) Filed: Aug. 15, 2006

(65) Prior Publication Data
US 2007/0047791 A1 Mar. 1, 2007

(30) Foreign Application Priority Data
Aug. 18, 2005 (DE) ........................ 10 2005 039 184

(51) Int. Cl.
*A61B 5/05* (2006.01)
(52) U.S. Cl. ..................... 600/407; 600/436; 128/922
(58) Field of Classification Search ................ 600/407, 600/436; 128/922; 345/418
See application file for complete search history.

(56) References Cited

U.S. PATENT DOCUMENTS

| | | | | |
|---|---|---|---|---|
| 5,803,914 | A * | 9/1998 | Ryals et al. | ................. 600/407 |
| 2003/0153823 | A1 | 8/2003 | Geiser et al. | |
| 2004/0162482 | A1 | 8/2004 | Assmann et al. | |
| 2005/0018895 | A1 | 1/2005 | Kawano | |

FOREIGN PATENT DOCUMENTS

| | | |
|---|---|---|
| DE | 103 31 098 A1 | 2/2005 |
| WO | WO 01/20305 | 3/2001 |

OTHER PUBLICATIONS

Sester RM, Kim JK, Chung YC et al (2006) Cine delayed-enhancement MR imaging of the heart: initial experience. Radiology 239:856-862.*
Sester RM, Kim JK, Chung YC et al (2006) Cine delayed enhancement imaging of the heart. Proc. Intl. Soc. Mag. Reson. Med. 13 (2005).*
"Cine Delayed Enhancement Imaging of the Heart," Seter et al., Proc. Intl. Soc. Mag. Reson. Med., vol. 13 (2005) p. 236.

* cited by examiner

*Primary Examiner*—Long V Le
*Assistant Examiner*—Nigel Fontenot
(74) *Attorney, Agent, or Firm*—Schiff Hardin LLP

(57) ABSTRACT

In a method and magnetic resonance tomography apparatus for evaluation of a cinematographic image series of the heart during a heart cycle, wherein the image series is acquired with an acquisition unit, and in the image series healthy heart muscle tissue is presented as differentiable from damaged heart muscle tissue, at least two individual images of the image series are processed in a data processing unit, with at least one region of the healthy heart muscle and/or of the damaged heart muscle being detected in each of the individual images by a pattern recognition algorithm, and at least one descriptive quantity is measured that describes a geometric property of the region that has been detected by the pattern recognition algorithm, a dynamic change of the descriptive quantity is detected, and medically-relevant information that is acquired from the dynamic change of the descriptive quantity is made available as an output.

16 Claims, 2 Drawing Sheets

METHOD AND MRT APPARATUS FOR EVALUATION OF A CINEMATOGRAPHIC IMAGE SERIES OF THE HEART

BACKGROUND OF THE INVENTION

1. Field of the Invention

The present invention concerns a method and a magnetic resonance tomography (MRT) apparatus for evaluation of a cinematographic image series of the heart in which healthy heart muscle tissue is shown so as to be differentiable from damaged heart muscle tissue, in particular in a cine delayed enhancement MRT image series of the heart.

2. Description of the Prior Art

In Proc. Intl. Soc. Mag. Reson. Med. 13, p. 236 (2005), a method is described in which a cinematographic or cine image series of the heart acquired by MRT using a TrueFISP sequence 10 to 20 minutes after an intravenous application of gadopentate dimeglumine. This image series is called as a cine delayed enhancement image series. An image series of the heart is thereby obtained during a heart cycle in which ischemia-damaged heart muscle tissue is made visible by a contrast agent administration. The evaluation of such an image series has conventionally ensued manually by the user, which is associated with a high personnel and time expenditure. The expansion of the scar tissue and the contractility of the entire heart wall are thereby quantified.

SUMMARY OF THE INVENTION

An object of the present invention is to provide a method with which an image series of the heart during a heart cycle, in which healthy heart muscle tissue is shown so as to be differentiable from damaged heart muscle tissue, is automatically evaluated at least in significant portions, and medically-relevant information regarding the degree of the damage are output to the user.

This object is achieved according to the invention by a method for evaluation of a cinematographic image series of the heart during a heart cycle, wherein the image series is acquired with an acquisition unit, and in the image series healthy heart muscle tissue is presented as differentiable from damaged heart muscle tissue, at least two individual images of the image series are processed in a data processing unit, with at least one region of the healthy heart muscle and/or of the damaged heart muscle being detected in each of the individual images by a pattern recognition algorithm, and at least one descriptive quantity is measured that describes a geometric property of the region that has been detected by the pattern recognition algorithm, a dynamic change of the descriptive quantity is detected, and medically-relevant information that is acquired from the dynamic change of the descriptive quantity is made available as an output.

By this method, for the evaluation of the image series essential and work-intensive steps that previously required a manual evaluation are resolved semi-automatically or automatically such that time and costs are saved. The descriptive quantity characterizes geometric information of the region detected by the pattern recognition algorithm and, for example, can be a diameter, the width or the area of the region. The pattern recognition algorithm can operate automatically or semi-automatically. For example, by using an automatic segmentation algorithm, the well-differentiable contrast agent-free and contrast agent-marked regions of the heart muscle can be detected and marked if applicable. In an interactive embodiment of the segmentation algorithm, the user can establish points that serve as start points for the segmentation algorithm and, if applicable, manually intervene and effect corrections. The pattern recognition algorithm does not necessarily have to be fashioned as a segmentation algorithm. For example, it can be sufficient for the pattern recognition algorithm to characterize the beginning and the end of contrast agent-marked or contrast agent-free regions along predetermined lines (such as along section lines) and marks them if applicable. It is thereby possible to determine diameters of regions.

Since the evaluation occurs in at least two images of the image series, the change of the descriptive quantity can be tracked over the heart cycle. From the dynamic change of the quantity medically-relevant information can be acquired whose information content exceeds that which would result from the evaluation of a single static image. The information is subsequently output to the user.

In a preferred embodiment, the medically-relevant information is a graphical and/or a tabular representation of the dynamic change of the descriptive quantity. The user can thereby quantitatively recognize at a glance how the descriptive quantity has changed over the time of the heart cycle.

A value from the dynamic change of the descriptive quantity that belongs to a specific point in time is output as medically-relevant information. The point in time can be a particularly characteristic point in time during the heart cycle such as, for example, the point in time of the end systole or of the end diastole.

In a further embodiment of the invention, the medically-relevant information is the percentage change of the quantity between two specific points in time (such as, for example, the end systole and the end diastole). The user thus can be informed in a simple manner about the change of the specific quantity during the heart cycle.

In a further embodiment of the invention, the medically-relevant information is a maximum value or a minimum value from the dynamic change of the descriptive quantity or the percentage change of the descriptive quantity with regard to the maximum value or minimum value. The user is informed in a simple and concise manner about the change of the determined quantity (for example about the radial diameter of the infarct scar) during the heart cycle.

In a preferred embodiment, the cinematographic image series is a short axis section series of the heart. However, depending on the clinical question an image series of another slice plane can also be selected, for example a longitudinal axis section or a four chamber section series.

In the short axis section series a radius in a specific direction is established and a radial diameter of the healthy heart muscle along the radius is measured. The percentage change of the heart muscle thickness of the healthy heart muscle during a heart cycle is determined therefrom. From this information the user can detect the contractility that the healthy heart muscle has in the direction of the radius. This information allows conclusions about the remaining contractility and the vitality of healthy heart muscle tissue, primarily in regions of the heart muscle in which both healthy and damaged heart muscle tissue are present, and can play a decisive role for a further therapy planning.

In a further embodiment of the invention, a number of radii are established in different directions and a direction-dependent percentage change of the heart muscle thickness of the healthy heart muscle is detected with regard to each of these radii. Information about the spatial distribution of contractility and contractility decreases can thereby be acquired. The direction-dependent percentage change of the heart muscle thickness is preferably represented in a bull's-eye plot in order to supply the user with a graphically-concise representation of the medically-important information. The bull's-eye plot can be color-coded.

In a further embodiment, as in the measurement of the healthy heart muscle, a radial diameter of the damaged heart muscle is measured along a radius in a specific direction. The percentage change of the heart muscle thickness of the damaged heart muscle along this radius is advantageously determined during a heart cycle. The user thereby obtains a conclusion about the remaining contractility that is possibly still present or about a possible imminent heart wall rupture. Here a number of radii in different directions can also be established along which the percentage change of the heart muscle thickness of the damaged heart muscle is respectively detected. Information about the spatial expansion of the damaged heart muscle tissue can be acquired. The representation preferably ensues in a bull's-eye plot that can be color-coded.

In a preferred embodiment, the cinematographic image series of the heart is a cine delayed enhancement MRT series since healthy and damaged heart muscle tissue are shown in a well-differentiable manner in this series. Other image series of the heart are also suitable as long as healthy and damaged heart muscle tissue are shown in a differentiable manner. For example, this can also be achieved with a Gated SPECT CT representation of the heart.

The above object also is achieved in accordance with the present invention by a magnetic resonance tomography apparatus operated in accordance with the procedure described above.

The above object also is achieved in accordance with the present invention by a computer-readable medium encoded with program code that is loadable into a control computer of a magnetic resonance tomography apparatus and, when executed, causes the magnetic resonance tomography apparatus to be operated according to the procedure described above.

DESCRIPTION OF THE PREFERRED EMBODIMENTS

Figure 1:
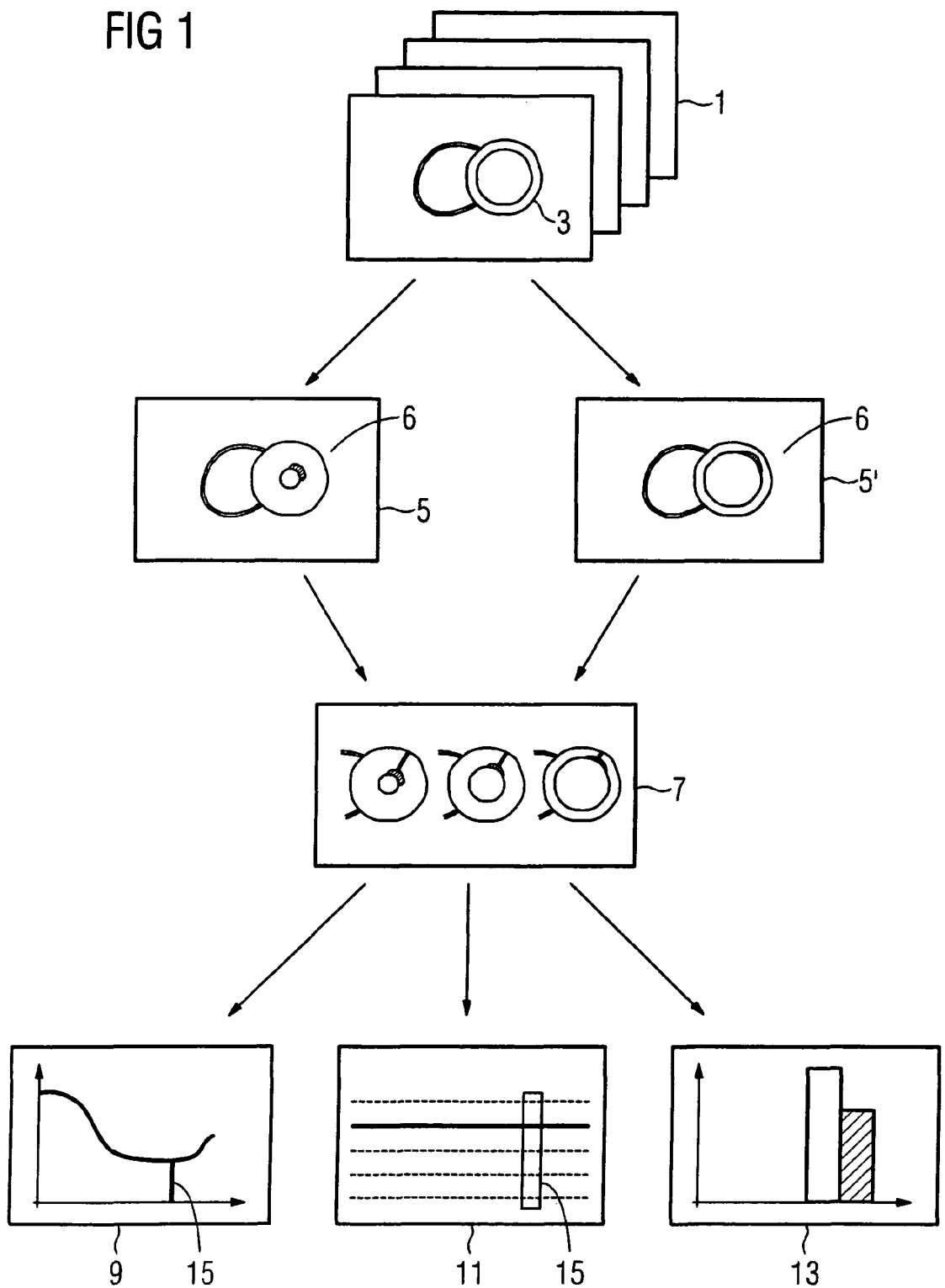
FIG. 1 schematically illustrates a workflow embodiment of the inventive method.

FIG. 1 schematically shows an embodiment of the workflow for the evaluation of a cinematographic image series 1 of the heart 3 during a heart cycle in accordance with the invention. The starting point is an image series 1 of the heart 3 during a heart cycle. The image series 1 is advantageously a cine delayed enhancement MRT series. In this series 1, contrast agent notably accumulates in damaged heart muscle tissue and thus generates a strong contrast between damaged and healthy heart muscle tissue such that a pattern recognition algorithm 6 can reliably differentiate between regions with damaged and healthy heart muscle tissue.

The pattern recognition algorithm 6 is applied to all individual images of the series 5, 5'. The regions of healthy and/or damaged heart muscle can thereby be detected and their variation can be tracked across the entire heart cycle. In practice, it is for the most part sufficient when the variation of a specific quantity that describes the geometry of the regions is tracked instead of the variation of the regions. For example, the variation of a radial diameter of healthy heart muscle tissue during a heart cycle possesses a high significance regarding the contractility and therewith also about the vitality of the healthy heart muscle tissue. After the individual images 5, 5' have been processed with the pattern recognition algorithm 6, the dynamic change 7 of the specific quantity is therefore detected as it is described in detail using FIGS. 2, 3 and 4.

It is often advantageous to form a number of quantities that describe geometric properties of different regions in the heart muscle. For example, at one point of the heart the inner layer of the heart muscle can contain damaged heart muscle tissue while the outer layer of the heart muscle is still intact. In this case it is advantageous to determine two quantities, of which one describes the diameter of the healthy heart muscle and the other describes the diameter of the damaged heart muscle. These two quantities can be set in relation to one another in order, for example, to determine their percentage proportions of the entire diameter of the heart muscle.

In a further step, medically-relevant information is output to the user that results from the dynamic change 7 of the quantity. This can be, for example, a graphical representation 9 of the change of the specific quantity itself or a tabular representation 11. It is thereby advantageous for values 15 that belong to characteristic points in time of the heart cycle to be identified separately. Percentage and/or absolute values 13 that characterize the change of the specific quantity during a heart cycle can also be determined from the dynamic change 7.

Figure 2:
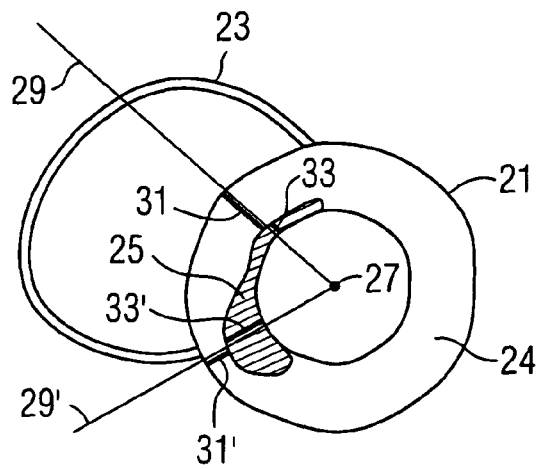
FIG. 2 schematically shows an image of a short axis section series of the heart at the point in time of the end systole.

FIG. 2 schematically shows a short-axis section of the heart at the point in time of the end systole. The heart muscle of the left ventricle 21 and the heart muscle of the right ventricle 23 are contracted. The damaged heart muscle tissue 25 is located on the inner layer of the heart and is surrounded by healthy heart muscle tissue 24. In this specific example the pattern recognition algorithm draws two radii 29 and 29' in two different directions from a central point 27 in the left ventricle 21. Along both of these radii 29 and 29' the pattern recognition algorithm respectively detects the regions of the healthy heart muscle and the damaged heart muscle, the radial diameters 31, 31' or 33, 33' of which can then be measured.

Figure 3:
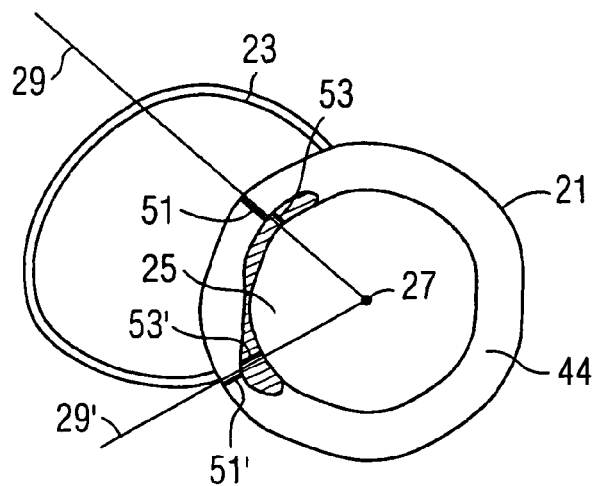
FIG. 3 schematically shows an image of a short axis section series of the heart at the point in time of the end diastole.

A further short axis section of the heart is schematically shown in FIG. 3 from the same cinematographic image series of the heart from which FIG. 2 is taken, and in fact at the point in time of the end diastole. The heart muscle of the left ventricle 21 and of the right ventricle 23 is relaxed. In this image the regions of the healthy heart muscle and the damaged heart muscle are also detected along the same radii 29 and 29' that emanate from the same start point 27. The radial diameters 51, 51' characterize the thickness of the healthy heart muscle tissue, the radial diameters 53, 53' characterize the thickness of the damaged heart muscle tissue.

While the radial diameters of the healthy heart muscle 31 and 51 notably change along the radius 29 between end systole and end diastole, the radial diameters 31' and 51' along the radius 29' remain largely the same. This means that in this specific example the contractility of the heart muscle tissue is clearly limited along the radius 29'. This information can play a decisive role for a further therapy planning such as for a rechannelization of the corresponding coronary artery.

Figure 4:
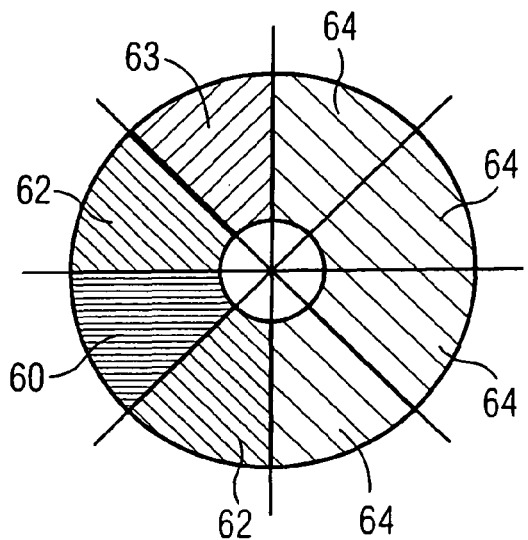
FIG. 4 shows a bull's-eye plot for identification of the contractility of the healthy heart muscle.

FIG. 4 shows a bull's-eye plot consistent with FIG. 2 and FIG. 3 in which the contractility of the healthy heart muscle is coded in various radial directions. This is one possible representation form of the results that enables the user to localize function limitations of the heart muscle in a particularly simple manner. In the bull's-eye plot shown here the heart muscle has bee divided into eight octants. The contractility of the healthy heart muscle tissue (corresponding to the localization of the radius 29') is severely limited in region 60 while the heart muscle tissue contracts normally in the regions 64. In the intermediate regions 62 (corresponding to the radius 29) and 63 the contractility of the heart muscle is in fact limited, but not to the degree as in region 60.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for evaluating a cinematographic image series of a heart during a heart cycle thereof, comprising the steps of:
    acquiring a cinematographic short axis image series of a heart beating through a heart cycle with an image acquisition unit using an image acquisition modality that causes healthy heart muscle tissue to be represented in said image series in a manner differentiatable from damaged heart muscle tissue, said image series being comprised of a plurality of individual images;
    processing at least two of said individual images by executing a pattern recognition algorithm in a data processor, to detect, in each individual image, at least one region, as a detected region, consisting of both a region of healthy heart muscle and a region of damaged heart muscle and to differentiate between said region of healthy heart muscle and said region of damaged heart muscle;
    within the detected region of each of said two of said individual images, automatically electronically measuring in said data processor, a radial diameter of only the region of healthy heart muscle;
    in said data processor, automatically electronically detecting a dynamic change of said radial diameter of said region of healthy heart muscle in said at least two of said individual images in said image series; and
    in said data processor automatically electronically generating medically-relevant information based on said dynamic change of said radial diameter of said region of healthy heart muscle and making said medically-relevant information available in a humanly perceptible form.

2. A method as claimed in claim 1 comprising making said medically-relevant information available in a humanly perceptible form comprises displaying said medically-relevant information in a display representation selected from the group consisting of a graphical representation of said dynamic change of said radial diameter of said region of healthy heart muscle and a tabular representation of said dynamic change of said radial diameter of said region of healthy heart muscle.

3. A method as claimed in claim 1 wherein the step of making said medically-relevant information available in humanly perceptible form comprises emitting a value of said dynamic change of said radial diameter of said region of healthy heart muscle at a specific point in time.

4. A method as claimed in claim 1 wherein the step of making said medically-relevant information available in humanly perceptible form comprises emitting a value of a percentage change of said radial diameter of said region of healthy heart muscle between two specific points in time.

5. A method as claimed in claim 4 comprising selecting said two specific points in time as end systole and end diastole, respectively.

6. A method as claimed in claim 1 wherein the step of making said medically-relevant information available in humanly perceptible form comprises emitting at least one of a maximum value of said dynamic change of said radial diameter of said region of healthy heart muscle and a minimum value of said dynamic change of said radial diameter of said region of healthy heart muscle.

7. A method as claimed in claim 1 wherein the step of making said medically-relevant information available in humanly perceptible form comprises emitting a value indicating a percentage change of at least one of said maximum value of said dynamic change of said radial diameter of said region of healthy heart muscle and a percentage change of said minimum of said dynamic change of said radial diameter of said region of healthy heart muscle.

8. A method as claimed in claim 1 comprising, in said data processor, automatically electronically, or by user interaction with said data processor, establishing a plurality of radii in respectively different directions in said short axis section series, and measuring, along each of said radii, a direction-dependent percentage change of a thickness of said healthy heart muscle.

9. A method as claimed in claim 8 wherein the step of making said medically-relevant information available in a humanly perceptible form comprises graphically representing the direction-dependent percentage change of said thickness of said healthy heart muscle respectively along said radii in a bull's-eye plot.

10. A method as claimed in claim 1 comprising, in said data processor, automatically electronically, or by user interaction with said data processor, establishing a radius in said short axis section series and measuring, as said at least one descriptive quantity, a radial diameter of said damaged heart muscle along said radius.

11. A method as claimed in claim 10 comprising measuring, as a further descriptive quantity, a percentage change in thickness of said damaged heart muscle along said radius during a heart cycle.

12. A method as claimed in claim 1 comprising, in said data processor, automatically electronically, or by user interaction with said data processor, establishing a plurality of radii in respectively different directions in said short axis section series, and also measuring, along each of said radii, a direction-dependent percentage change of a thickness of said damaged heart muscle.

13. A method as claimed in claim 12 wherein the step of making said medically-relevant information available in a humanly perceptible form comprises graphically representing the direction-dependent percentage change of said thickness of said damaged heart muscle respectively along said radii in a bull's-eye plot.

14. A method as claimed in claim 1 comprising acquiring said cinematographic image series with a magnetic resonance tomography apparatus as a cine late enhancement MRT series.

15. A magnetic resonance tomography apparatus for evaluating a cinematographic image series of a heart during a heart cycle thereof, comprising:
    a magnetic resonance image acquisition unit adapted to interact with a subject to acquire a cinematographic short axis image series of a heart of the subject beating through a heart cycle, using an image acquisition modality that causes healthy heart muscle tissue to be represented in said image series in a manner differentiatable from damaged heart muscle tissue, said image series being comprised of a plurality of individual images;

a processor configured to process at least two of said individual images by executing a pattern recognition algorithm to detect, in each individual image, at least one region, as a detected region, consisting of both a region of healthy heart muscle and a region of damaged heart muscle, and to differentiate between said region of healthy heart muscle and said region of damaged heart muscle and, within the detected region of each of said two of said individual images, to automatically measure a radial diameter of only said region of healthy heart muscle;

said processor being configured to automatically detect a dynamic change of said radial diameter of said region of healthy heart muscle in said at least two of said individual images in said image series; and a display connected to said processor, automatically generating medically-relevant information based on said dynamic change of said radial diameter of said region of healthy heart muscle and making said medically-relevant information available at said display.

16. A non-transitory computer-readable medium encoded with program data leadable into a control and data processing computer of a magnetic resonance tomography apparatus for causing said apparatus to:

acquire a cinematographic short axis image series of a heart beating through a heart cycle with an image acquisition unit of the apparatus using an image acquisition modality that causes healthy heart muscle tissue to be represented in said image series in a manner differentiatable from damaged heart muscle tissue, said image series being comprised of a plurality of individual images;

process at least two of said individual images by executing a pattern recognition algorithm in a data processor of the apparatus, to detect, in each individual image, at least one region, as a detected region, consisting of both a region of healthy heart muscle and a region of damaged heart muscle and to differentiate between said region of healthy heart muscle and said region of damaged heart muscle and, within the detected region of each of said two of said individual images, to automatically electronically measure a radial diameter of only said region of healthy heart muscle;

automatically electronically detect a dynamic change of said radial diameter of said region of healthy heart muscle in said at least two of said individual images in said image series; and automatically electronically generate medically-relevant information based on said dynamic change of said radial diameter of said region of healthy heart muscle and make said medically-relevant information available in a humanly perceptible form.

* * * * *